(12) United States Patent
Merrill et al.

(10) Patent No.: US 6,376,729 B1
(45) Date of Patent: Apr. 23, 2002

(54) MULTI-PHASE ALKYLATION PROCESS

(75) Inventors: James T. Merrill, Katy; James R. Butler, Houston, both of TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 09/729,032

(22) Filed: Dec. 4, 2000

(51) Int. Cl.$^7$ ............................ C07C 2/66; C07C 15/073
(52) U.S. Cl. ........................ 585/449; 585/467; 585/323
(58) Field of Search ..................... 585/444, 467, 585/323, 470

(56) References Cited

U.S. PATENT DOCUMENTS

| | | | |
|---|---|---|---|
| 4,107,224 A | 8/1978 | Dwyer | 585/44 Y |
| 4,169,111 A | 9/1979 | Wight | 585/323 |
| 4,185,040 A | 1/1980 | Ward et al. | 585/467 |
| 4,489,214 A | 12/1984 | Butler et al. | 585/467 |
| 4,642,226 A | 2/1987 | Calvert et al. | 423/328 |
| 4,774,377 A | 9/1988 | Barger et al. | 585/323 |
| 4,781,906 A | 11/1988 | Cahen et al. | 423/328 |
| 4,922,053 A | 5/1990 | Waguespack et al. | 585/446 |

FOREIGN PATENT DOCUMENTS

| | | |
|---|---|---|
| EP | 467007 | 1/1992 |
| EP | 507761 | 7/1992 |

*Primary Examiner*—Walter D. Griffin
*Assistant Examiner*—Thuan D. Dang
(74) *Attorney, Agent, or Firm*—William D. Jackson

(57) ABSTRACT

A process for the production of ethylbenzene by the gas phase alkylation of benzene over a molecular sieve aromatic alkylation catalyst followed by liquid phase alkylation of the product of the gas phase alkylation. A feedstock containing benzene and ethylene is supplied to a first alkylation reaction zone containing a molecular sieve aromatic alkylation catalyst. The reaction zone is operated at temperature and pressure conditions to cause gas phase ethylation of the benzene with the production of an alkylation product comprising a mixture of ethylbenzene and polyalkylated aromatic components including diethylbenzene. The output from the first alkylation reaction zone is supplied, at least in part, to a second alkylation zone which is operated in the liquid phase or in the supercritical region followed by supply to an intermediate recovery zone for the separation and recovery of ethylbenzene and a polyalkylated aromatic compound component including diethylbenzene.

20 Claims, 3 Drawing Sheets

MULTI-PHASE ALKYLATION PROCESS

FIELD OF THE INVENTION

This invention involves an aromatic alkylation/transalkylation process involving vapor phase ethylation of benzene over a molecular sieve alkylation catalyst followed by liquid phase alkylation of the vapor phase reaction output followed by separate transalkylation.

BACKGROUND OF THE INVENTION

Aromatic conversion processes which are carried out over molecular sieve catalyst are well known in the chemical processing industry. Such aromatic conversion reactions include the alkylation of aromatic substrates such as benzene to produce alkyl aromatics such as ethylbenzene, ethyltoluene, cumene or higher aromatics and the transalkylation of polyalkyl benzenes to monoalkyl benzenes. Typically, an alkylation reactor which produces a mixture of mono- and polyalkyl benzenes may be coupled through various separation stages to a downstream transalkylation reactor. Such alkylation and transalkylation conversion processes can be carried out in the liquid phase, in the vapor phase or under conditions in which both liquid and vapor phases are present.

Alkylation and transalkylation reactions may occur simultaneously within a single reactor. For example, where various series-connected catalyst beds are employed in an alkylation reactor as described below, it is a conventional practice to employ interstage injection of the aromatic substrate between the catalyst beds, which tends to enhance transalkylation reactions within the alkylation reactor. For example, in the ethylation of benzene with ethylene to produce ethylbenzene, the alkylation product within the reactor includes not only ethylbenzene but also polyethylbenzene, principally diethylbenzene with reduced amounts of triethylbenzene, as well as other alkylated aromatics such as cumene and butylbenzene. The interstage injection of the ethylene results not only in further in alkylation reactions but also in transalkylation reactions where, for example, benzene and diethylbenzene undergo transalkylation to produce ethylbenzene. Thus, even though a separate transalkylation reactor is connected downstream through a series of separation stages, it is the accepted practice to minimize polyalkylation within the alkylation reactor in order to facilitate the subsequent treatment and separation steps.

An example of vapor phase alkylation is found in U.S. Pat. No. 4,107,224 to Dwyer. Here, vapor phase ethylation of benzene over a zeolite catalyst is accomplished in a down flow reactor having four series connected catalyst beds. The output from the reactor is passed to a separation system in which ethylbenzene product is recovered, with the recycle of polyethylbenzenes to the alkylation reactor where they undergo transalkylation reactions with benzene. The catalysts used in Dwyer are characterized in terms of those having a constraint index within the approximate range of 1–12 and include, with the constraint index in parenthesis, ZSM-5 (8.3), ZSM-11 (8.7), ZSM-12 (2), ZSM-35 (4.5), ZSM-38 (2), and similar materials.

The molecular sieve, silicalite, is a well-known alkylation catalyst. For example, U.S. Pat. No. 4,520,220 to Watson et al discloses the use of silicalite catalysts having an average crystal size of less than 8 microns and a silica/alumina ratio of at least about 200 in the ethylation of an aromatic substrate such as benzene or toluene to produce ethylbenzene or ethyltoluene, respectively. As disclosed in Watson et al, the alkylation procedure can be carried out in a multi-bed alkylation reactor at temperatures ranging from about 350°–500° C. and, more desirably, about 400°–475° C., with or without a steam co-feed. The reactor conditions in Watson et al are such as to provide generally for vapor phase alkylation conditions.

Another procedure employing silicalite and involving the ethylation of benzene under vapor phase reaction conditions coupled with the recycle of polyethylbenzene containing products back to the alkylation reactor is disclosed in U.S. Pat. No. 4,922,053 to Wagnespack. Here, alkylation is carried out at temperatures generally in the range of 370° C. to about 470° C. and pressures ranging from atmospheric up to about 25 atmospheres over a catalyst such as silicalite or ZSM-5. The catalysts are described as being moisture sensitive and care is taken to prevent the presence of moisture in the reaction zone. The alkylation/transalkylation reactor comprises four series connected catalyst beds. Benzene and ethylene are introduced into the top of the reactor to the first catalyst bed coupled by recycle of a polyethylbenzene fraction to the top of the first catalyst bed as well as the interstage injection of polyethylbenzene and benzene at different points in the reactor.

Another process involving the use of a silicalite as an alkylation catalyst involves the alkylation of an alkylbenzene substrate in order to produce dialkylbenzene of a suppressed ortho isomer content. Thus, as disclosed in U.S. Pat. No. 4,489,214 to Butler et al, silicalite is employed as a catalyst in the alkylation of a monoalkylated substrate, toluene or ethylbenzene, in order to produce the corresponding dialkylbenzene, such as ethyl toluene or diethylbenzene. Specifically disclosed in Butler et al is the ethylation of toluene to produce ethyltoluene under vapor phase conditions at temperatures ranging from 350°–500° C. As disclosed in Butler, the presence of ortho ethyltoluene in the reaction product is substantially less than the thermodynamic equilibrium amount at the vapor phase reaction conditions employed.

U.S. Pat. No. 4,185,040 to Ward et al discloses an alkylation process employing a molecular sieve catalyst of low sodium content which is said to be especially useful in the production of ethylbenzene from benzene and ethylene and cumene from benzene and propylene. The $Na_2O$ content of the zeolite should be less than 0.5 wt. %. Examples of suitable zeolites include molecular sieves of the X, Y, L, B, ZSM-5, and omega crystal types, with steam stabilized hydrogen Y zeolite being preferred. Specifically disclosed is a steam stabilized ammonium Y zeolite containing about 0.2% $Na_2O$. Various catalyst shapes are disclosed in the Ward et al patent. While cylindrical extrudates may be employed, a particularly preferred catalyst shape is a so-called "trilobal" shape which is configured as something in the nature of a three leaf clover. The surface area/volume ratio of the extrudate should be within the range of 85–160 $in.^{-1}$. The alkylation process may be carried out with either upward or downward flow, the latter being preferred, and preferably under temperature and pressure conditions so that at least some liquid phase is present, at least until substantially all of the olefin alkylating agent is consumed. Ward et al state that rapid catalyst deactivation occurs under most alkylating conditions when no liquid phase is present.

U.S. Pat. No. 4,169,111 to Wight discloses an alkylation/transalkylation process for the manufacture of ethylbenzene employing crystalline aluminosilicates in the alkylation and transalkylation reactors. The catalysts in the alkylation and transalkylation reactors may be the same or different and include low sodium zeolites having silica/alumina mole ratios between 2 and 80, preferably between 4–12. Exemplary zeolites include molecular sieves of the X, Y, L, B, ZSM-5 and omega crystal types with steam stabilized Y zeolite containing about 0.2% $Na_2O$ being preferred. The alkylation reactor is operated in a downflow mode and under temperature and pressure conditions in which some liquid phase is present. The output from the alkylating reactor is cooled in a heat exchanger and supplied to benzene separation columns from which benzene is recovered overhead and recycled to the alkylation reactor. The initial higher boiling bottoms fraction from the benzene columns comprising ethylbenzene and polyethylbenzene is supplied to an initial ethylbenzene column from which the ethylbenzene is recovered as the process product. The bottoms product from the ethylbenzene column is supplied to a third column which is operated to provide a substantially pure diethylbenzene overheads fraction which contains from 10 to 90%, preferably 20 to 60% of diethylbenzene. The diethylbenzene overheads fraction is recycled to the alkylation reactor, while a side cut containing the remaining diethylbenzene and triethylbenzene and higher molecular weight compounds is supplied to the reactor along with benzene. The effluent from the reactor is recycled through the heat exchanger to the benzene column.

U.S. Pat. No. 4,774,377 to Barger et al discloses an alkylation/transalkylation process which, involves the use of separate alkylation and transalkylation reaction zones, with recycle of the transalkylated product to an intermediate separation zone. In the Barger process, the temperature and pressure conditions are adjusted so that the alkylation and transalkylation reactions take place in essentially the liquid phase. The transalkylation catalyst is an aluminosilicate molecular sieve including X-type, Y-type, ultrastable-Y, L-type, omega type and mordenite type zeolites with the latter being preferred. The catalyst employed in the alkylation reaction zone is a solid phosphoric acid containing material. Aluminosilicate alkylation catalysts may also be employed and water varying from 0.01 to 6 volume percent is supplied to the alkylation reaction zone. The output from the alkylation reaction zone is supplied to first and second separation zones. Water is recovered in the first separation zone. In the second separation zone, intermediate aromatic products and trialkylaromatic and heavier products are separated to provide an input to the transalkylation reaction zone having only dialkyl aromatic components, ie. diethylbenzene in the case of an ethylbenzene manufacturing procedure or diisopropylbenzene in the case of cumene production. A benzene substrate is also supplied to the transalkylation zone for the transalkylation reaction and the output from the transalkylation zone is recycled to the first separation zone. The alkylation and transalkylation zones may be operated in downflow, upflow, or horizontal flow configurations.

EPA publication 467,007 to Butler discloses other processes having separate alkylation and transalkylation zones employing various molecular sieve catalysts and with the output from the transalkylation reactor being recycled to an intermediate separation zone. Here, a benzene separation zone, from which an ethylbenzene/polyethylbenzene fraction is recovered from the bottom with recycling of the overhead benzene fraction to the alkylation reactor is preceded by a prefractionation zone. The prefractionation zone produces an overhead benzene fraction which is recycled along with the overheads from the benzene column and a bottom fraction which comprises benzene, ethylbenzene and polyethylbenzene. Two subsequent separation zones are interposed between the benzene separation zone and the transalkylation reactor to provide for recovery of ethylbenzene as the process product and a heavier residue fraction. The polyethylbenzene fraction from the last separation zone is applied to the transalkylation reactor and the output there is applied directly to the second benzene separation column or indirectly through a separator and then to the second benzene separation column. Butler discloses that the alkylation reactor may be operated in the liquid phase with a catalyst such as zeolite-$\beta$, zeolite-Y or zeolite-$\Omega$ or in the vapor phase employing a catalyst such as silicalite or ZSM-5. In the Butler process, where vapor phase alkylation is followed by liquid phase transalkylation, substantial quantities of water may be included in the feedstream to the alkylation reactor. In this case, the feed to the transalkylation reactor may be dehydrated to lower the water content. The transalkylation catalyst may take the form of a zeolite-Y or zeolite-$\Omega$.

SUMMARY OF THE INVENTION

In accordance with the present invention there is provided a process for the production of ethylbenzene by the alkylation of benzene over a molecular sieve aromatic alkylation catalyst, preferably monoclinic silicalite having a silica/alumina ratio of at least 275, followed by liquid phase alkylation and followed in turn by transalkylation of polyalkylated aromatic components. In carrying out the invention, a feedstock containing benzene and ethylene is supplied to a first alkylation reaction zone containing a molecular sieve aromatic alkylation catalyst. The reaction zone is operated at temperature and pressure conditions to maintain the benzene in the gaseous phase and to cause gas phase ethylation of the benzene with the production of an alkylation product comprising a mixture of ethylbenzene and polyalkylated aromatic components including diethylbenzene with xylene present in only small amounts. All or part of the product from the first alkylation zone is supplied to a second alkylation reaction zone along with an additional supply of ethylene. The second alkylation reaction zone is operated at temperature and pressure conditions to maintain the benzene in the liquid phase or to maintain the benzene in the supercritical phase. The second alkylation reaction zone contains a molecular sieve catalyst, preferably an intermediate pore size molecular sieve selected from the group of zeolite-Y, zeolite omega, zeolite beta, and zeolite lanthanum beta, and is operated under conditions to produce a mixture of benzene and ethylbenzene. The output from the second alkylation reaction zone is supplied to an intermediate recovery zone for the separation and recovery of ethylbenzene and the separation and recovery of a polyalkylated aromatic compound component including diethylbenzene. In a preferred embodiment of the invention at least a portion of the polyalkylated component is supplied along with benzene to a transalkylation reaction zone. The transalkylation reaction zone is operated, preferably in the liquid phase, to cause disproportionation of the polyalkylated aromatic fraction to produce a disproportionation product containing unreacted benzene and having a reduced diethylbenzene content and an enhanced ethylbenzene content. Preferably, the disproportionation product from the transalkylation zone is supplied to the intermediate recovery zone.

DETAILED DESCRIPTION OF THE INVENTION

Figure 1:
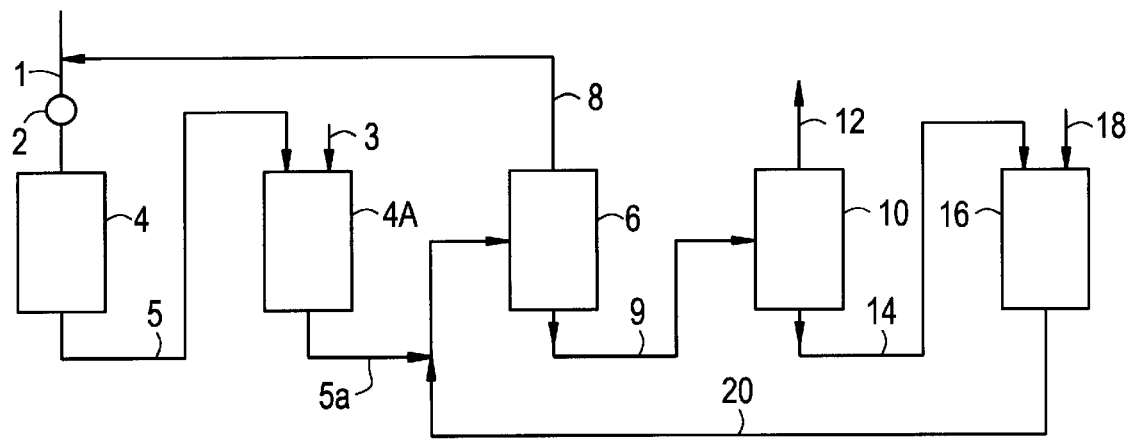
FIG. 1 is an idealized schematic block diagram of an alkylation/transalkylation alkylation process embodying the present invention.

The present invention involves the vapor phase alkylation of benzene over a silicalite alkylation catalyst, followed by a further alkylation procedure carried out in the liquid phase or in the supercritical region for benzene with subsequent recovery of ethlybenzene and transalkylation of a residual product. The preferred silicalite catalyst used in the vapor phase alkylation procedure provides for extremely low activity for the production of undesirable polyalkylated aromatics, specifically xylene and high boiling point alkyl aromatic components boiling at about 185° C. and above. In the production of ethylbenzene, the benzene substrate and the ethylene alkylating agent are injected in relative amounts so that the benzene is well in excess of the stoichiometric equivalent amount for the alkylation reaction. Under these circumstances, the ethylene constituent of the feedstream is the stoichiometric controlling reactant. That is, the ethylbenzene production rate can be increased by increasing the ethylene injection rate with an attendant reduction in the benzene/ethylene mole ratio or decreased by decreasing the ethylene injection rate with an attendant increase in the benzene/ethylene mole ratio. The foregoing assumes, of course, that the benzene feed rate remains constant. A difficulty encountered in increasing the ethylene flow rate, thus decreasing the benzene/ethylene ratio below a designated design perameter, is that the production of unwanted side products is often increased. A preferred embodiment of the present invention involves the use of an alkylation catalyst comprising a predominantly monoclinic silicalite of a high silica/alumina ratio, preferably one having a small crystal size, which enables the ethylene content of the feedstream to be materially increased with only a relatively small or even no increase in xylenes content and high boiling point polyalkylated aromatic components. Specifically, the catalyst can be characterized in terms of a xylene response to a 25% increase in ethylene rate (a decrease in the benzene/ethylene ratio of 20%) such that the increase in xylene production is no more than 10% relative to the production of ethylbenzene. Similarly, for the heavy polyalkylated aromatic components boiling at 185° C. or above, the corresponding increase under these conditions is no more than 5% relative to the production of ethylbenzene. The low xylene content in the effluent from the alkylation reactor is particularly significant in terms of the downstream separation of ethylbenzene since the xylenes, particularly the meta- and para-isomers having boiling points very close to the boiling point of ethylbenzene. Similarly, a low heavies content is desirable in terms of downstream separation procedures carried out prior to the supply of diethylbenzene, which has a maximum boiling point of about 185° C., to a downstream transalkylation reactor.

The practice of the present invention will normally follow the accepted practice of vapor phase alkylation of an aromatic substrate in a first alkylation reaction zone followed by a separate transalkylation reaction. However, rather than passing the product produced by vapor phase alkylation directly to an intermediate separation zone for the recovery of ethylbenzene and the recycle of benzene, a portion or part of this product is supplied to a second alkylation reactor which is operated in the liquid phase or optionally in the supercritical region for benzene. A preferred embodiment of the invention involves the use in the vapor phase alkylation procedure of a high silica/alumina ratio silicalite alkylation catalyst in a mode that actually increases the diethylbenzene output from the vapor phase alkylation reaction during a portion of a cycle of operation in which one of a plurality of parallel vapor phase reactors is placed in a regeneration mode. The alkylation reactor can be operated under a relatively high space velocity such that the alkylation over the silicalite catalyst is carried out to provide a diethylbenzene content substantially above what is achieved under normal operating conditions. Specifically, the diethylbenzene content is increased by incremental value of about 0.2 or more of the diethylbenzene content produced at a space velocity of one-half of the enhanced space velocity. This enhanced space velocity occurs during a relatively short period of time after which a reduced space velocity is encountered in which the diethylbenxene content is reduced during normal operating conditions to a value near the thermodynamic equilibrium value. The enhanced diethylbenzene production is offset by an accompanying selectivity toward the production of ethylbenzene relative to the production of xylenes as a by-product. Stated otherwise, the xylene content in the product is diminished preferably to a value of less than 0.6 wt. % based upon the ethylbenzene in the product. Further, the ortho xylene content is contained at a relatively low level, less than the thermodynamic equilibrium level of ortho xylene at temperature and pressure conditions of the alkylation reactor zone. Specifically, the ortho xylene content can be diminished to a value of about one-half or less than the equilibrium value. In this respect the equilibrium ratio of the three isomers of xylene at a desired alkylation temperature of about 400° C. is 24.3% ortho xylene, 52.3% meta xylene, and 23.4% para xylene. The practice of the present invention can result in a ortho xylene content in the reaction product of no more than 10 wt. % of the total xylene content of the reaction product.

The preferred silicalite employed in the vapor phase alkylation procedure, in addition to having a relative high silica aluminum ratio, has a smaller crystal size than the silicalite traditionally employed in a aromatic alkylation procedures. Silicalite, as is well known in the art, is a molecular sieve catlyst which is similar to the ZSM-5 zeolites but is typically characterized by a higher silica/alumina ratio providing an aluminum/unit cell ratio of less than 1, and, in addition, is normally characterized as having a somewhat larger than average crystal size than is commonly associated with the ZSM zeolites. As is well known in the art, silicalite, which in the as synthesized form is characterized by orthorhombic symmetry, can be converted to monoclinic symmetry by a calcination procedure as diclosed, for example, in U.S. Pat. No. 4,599,473 to DeBras et al. As described in detail in DeBras et al, "Physicochemical characterization of pentasil type materials, I. Precursors and calcined zeolites, and II. Thermnal analysis of the precursors," *Zeolites*, 1985, Vol. 5, pp. 369–383, the silicalite typically has a relatively large crystal size. Thus, at an average of less than one aluminum atom per unit cell (a silica/alumina ratio of about 200) silicalite typically has an average crystal size of perhaps 5–10 microns or more. The aforementioned U.S. Pat. No. 4,489,214 to Butler et al discloses experimental work involving the ethylation of toluene over silicalite of a crystal size greater than one micron, ranging from 1–2 microns up to 8 microns. The silicalite is further characterized in terms of a variable aluminum gradient such that the aluminum gradient is positive when going from the interior to the surface of the molecular sieve crystal. That is, the silicalite can be characterized by a core portion which is relatively aluminum deficient with an outer shell portion which is relatively aluminum rich. It is to be understood that the term "aluminum rich" is a relative term and that for silicalite even the outer shell portion of the crystallite has a low aluminum content.

As indicated previously, the output from the vapor phase alkylation reactor is supplied either entirely or in part to a second alkylation reactor which is designated as a liquid phase alkylation reactor. Normally the second alkylation reactor will be operated under pressure and temperature conditions in which the benzene or other aromatic substrate is in the liquid phase, that is, at temperature well below the critical temperature of benzene or other aromatic substrate with pressure sufficient to maintain the aromatic substrate in the liquid phase. However, since the subsequent alkylation reaction can be carried out under conditions in which the aromatic substrate is in the supercritical phase, i.e. at temperature and pressure conditions above the critical temperature and pressure, the term "liquid phase reactor," as used here and will be understood to denote a reactor operated in the supercritical region as well as in the liquid region. As described below, the molecular sieve catalyst used in the second liquid phase alkylation reactor will preferably have an effective pore size greater than the effective pore size of the molecular sieve catalyst in the first gas phase alkylation reactor.

The preferred embodiment of the present invention involves vapor phase ethylation of benzene in a multistage reaction zone containing high silica/alumina ratio silicalite followed by liquid phase alkylation, then followed in turn by liquid phase transalkylation with recycle of the disproportion product recovered from the transalkylation reactor to an intermediate recovery zone. The product from the liquid phase alkylation reactor is also supplied to the intermediate recovery zone. This zone preferably involves a plurality of separation zones operated in a manner to effectively provide feed streams to the reactors with recycle of the output from the transalkylation reactor to a benzene recovery zone downstream of the liquid phase alkylation reactor. In this integrated mode of operation, the transalkylation product is applied, along with the output from the second liquid phase reactor, to one or both stages of a multistage benzene recovery zone. Subsequent separation steps can be carried out in a manner to apply a split feed to the transalkylation reactor.

The vapor phase alkylation reactor is a multistage reaction zone containing at least three series connected catalyst beds which contain the silicalite alkylation catalyst. More preferably, four or more beds are employed. As described in greater detail below, the silicalite alkylation catalyst preferably is silicalite characterized as having a high monoclinicity and a small sodium content, both in terms of sodium in the crystalline molecular sieve structure and in the binder component. The preferred catalyst in the second liquid phase alkylation reactor is preferably zeolite Y or zeolite beta, with zeolite beta or zeolite La-Beta being particularly preferred. The preferred catalyst used in the transalkylation reactor is a molecular sieve also having a pore size greater than the pore size of the silicalite catalyst. Preferably, the transalkylation catalyst is zeolite Y.

The aforementioned zeolites are in themselves well known in the art. For example, zeolite Y is disclosed in the aforementioned U.S. Pat. No. 4,185,040 to Ward, and zeolite beta is disclosed in U.S. Pat. No. 3,308,069 to Wadlinger and U.S. Pat. No. 4,642,226 to Calvert et al. Zeolite lanthanum beta (LA-BETA) is disclosed in EPO Publication No. 507, 761 B1 to Shamshoum et al and may be prepared from zeolite beta by ion exchange to incorporate lanthanum into a precursor zeolite beta molecular sieve structure. For example, La-Beta can be prepared by ion exchange of anhydrous ammonium beta zeolite with an aqueous solution of lanthanum nitrate followed by mulling with nitrite acid-treated alumina, extrusion, and calcination. For a further description of zeolite Y, zeolite beta, and zeolite La-Beta, reference is made to the aforementioned U.S. Pat. No. 4,185,040 to Ward, U.S. Pat. No. 3,308,069 to Wadlinger, and U.S. Pat. No. 4,642,226 to Calvert et al and to EPO 507,761 B1 to Shamshoum et al, the entire disclosures of which are incorporated herein by reference.

A preferred application of the invention is in a system involving multistage alkylation reactors with the output from one or both alkylation reactors coupled to a four-stage separation system which in turn supplies a polyethylbenzene feed to a transalkylation reactor. In the embodiment of the invention described herein, two sets of parallel alkylation reactors (one set for vapor phase alkylation and the other set for liquid phase alkylation) and a set of parallel transalkylation reactors are employed. This results in a preferred mode of operation in which the parallel alkylation reactors are simultaneously operated in an alkylation mode while periodically one reactor can be taken off-stream with the feedstream completely supplied to the on-stream reactor. In the embodiment illustrated and described below, two parallel reactors are employed although it is to be recognized that three or more reactors can likewise be employed in parallel. A similar configuration is employed for the transalkylation reactors and for the liquid phase alkylation reactors. The result is that simultaneous catalyst regeneration can occur in one reactor during operation of the remaining alkylation and/or transalkylation reactors. Assuming that two parallel reactors are employed, it can be seen that this mode of operation will, for the same flow rate of feedstream, result in the operation of the reactors at two different space velocities, with the space velocity during regeneration of a reactor being about twice that with both parallel reactors in operation.

Preferably, the first vapor phase alkylation reactor comprises at least four catalyst beds as described above. More beds can be provided, and it will sometimes be advantageous to provide at least six catalyst beds in the alkylation reactor. The reactor is operated so as to provide vapor phase alkylation (both the aromatic substrate and the alkylating agent are in the vapor phase) at temperatures ranging from about 630° F.–800° F. at the inlet to about 700° F.–850° F. at the outlet. The pressure may be within the range of about 250 to 450 psia with the pressure decreasing from one bed to the next as the temperature increases. By way of example, the benzene and ethylene supplied to the top of the reactor may enter the reactor at a temperature of about 740° F. and a pressure of about 430 psia. The alkylation reaction is exothermic so that the temperature progressively increases from the first to the last catalyst bed by a way of example. The interstage temperatures may increase from 750° F. for the first catalyst bed to 765° F. after the second catalyst bed to 820° F. after the third catalyst bed to a temperature of about 840° F. after the last catalyst bed.

Normally in the operation of multi-stage reaction zone of the type involved in the present invention, a benzene-ethylene mixture is introduced to the first catalyst bed at the top of the reaction zone and also in between the several successive stages of catalyst beds. In the present invention, ethylene is supplied along with benzene to the top of the first catalyst bed top at the upper end of the reactor. In addition, interstage injection of ethylene and benzene is provided for between the subsequent catalyst beds. The benzene to ethylene mole ratio is about 18 as injected into the top of the alkylation reactor and progressively decreases because of the interstage injection of ethylene and coupled with the alkylation of the benzene to ethylbenzene and polyethylbenzenes.

The preferred silicalite alkylation catalyst employed in the initial vapor phase alkylation zone in the present invention does not require the presence of water to stabilize the catalyst, so a water or steam co-feed, as is sometimes used in connection with silicalite, is not called for in this invention. As noted above, interstage injection of ethylene is normally employed, and the interstage injection of benzene can also be provided for. The mole ratio of the benzene to the ethylene at the interstage injection points can vary from zero (no benzene injection) up to about five. The benzene in many cases will be employed in an amount less than the amount of ethylene on a mole basis. Stated otherwise, benzene can either not be injected between the catalyst beds or, if injected, can be employed in a relatively minor amount, ie., a mole ratio of benzene to ethylene of less than one. On the other hand, the benzene/ethylene mole ratio can be as high as five. This is coupled with a somewhat lower operating temperature than would normally be the case for vapor phase alkylation. In the preferred embodiment of the invention, the temperature of the benzene stream into the top of the alkylation reactor will be in the order of 720° F. or lower. The alkylation reaction is, of course, an exothermic reaction so that the temperature will be increased progressively throughout the alklylation column as noted previously.

The silicalite alkylation catalyst employed in the present invention is a molecular sieve from the pentasil family of high silica molecular sieves. Such pentasil molecular sieves are described, for example, in Kokotailo et al, "Pentasil Family of High Silica Crystalline Materials," Chem. Soc. Special Publ. 33, 133–139 (1980). The silicalite molecular sieve alkylation catalyst has a somewhat smaller pore size than the preferred zeolite-Y employed in the transalkylation reactor and the preferred zeolite beta (including La-Beta) used in the second liquid phase alkylation reactor. The silicalite catalyst has an effective pore size or window within the range of 5–6 angstroms. Zeolite Y has a pore size of about 7 angstroms. Zeolite beta has an elliptical pore having a major axis of about 7.5 angstroms and a minor axis of about 5.5 angstroms. Zeolite La-Beta has a pore size geometry similar to zeolite beta. The preferred silicalite catalyst has a somewhat smaller crystal size, less than one micron, than is usually the case. Preferably, the crystal size is even somewhat smaller, providing an average crystal size of about 0.5 $\mu$g or less, as contrasted with a crystal sizes of perhaps 1–2 $\mu$g up to about 8 microns for similar catalysts such as disclosed in the aforementioned U.S. Pat. No. 4,489,214 to Butler et al.

A preferred silicalite for use in the present invention is extruded with an alumina binder in a "trilobe" shape having a nominal diameter of about 1/16" and a length of the extrudate of about 1/8–1/4." As discussed below, the silicalite catalyst has a low sodium content and this is complemented in the preferred embodiment of the invention by the use of an alumina binder which is of unusually high purity and unusually large pore size as described in greater detail below. The "trilobe" cross sectional shape is something on the order of a three leaf clover. The purpose of this shape is to increase the geometric surface area of the extruded catalyst beyond what one would expect with a normal cylindrical extrudate. The silicalite catalyst is characterized as monoclinic silicalite. Monoclinic silicalite may be prepared as disclosed in U.S. Pat. No. 4,781,906 to Cahen et al and U.S. Pat. No. 4,772,456 to DeClippeleir et al. Preferably the catalysts will have near 100% monoclinicity) although silicalite catalysts that are 70–80% monoclinic and about 20–30% orthorhombic symmetry may be used in the preferred embodiment of the invention. The silicalite preferably is present in an amount of 75–80 wt. % with the alumina binder being present in an amount of 20–25 wt. %. The silica/alumina ratio of the silicalite is at least 250. An especially preferred silica/alumina ratio is 300–350, and silicalite within this range was used in experimental work respecting the invention as described hereafter. The silicalite may have an alpha value of about 20–30. The "alpha value" is characterized in terms of the activity of a catalyst for cracking hexane as disclosed in U.S. Pat. No. 4,284,529 to Shihabi and U.S. Pat. No. 4,559,314 to Shihabi. The silicalite catalyst typically contains small amounts of sodium and iron.

As noted previously, the silicalite alkylation catalyst has a crystal structure characterized by an aluminum rich outer shell and an aluminum deficient interior portion when compared with the outer shell. The silicalite catalyst is dry and has no appreciable or intended water content. Specifically, the silicalite catalyst contains no more than about 200 ppm sodium, preferably no more than 100 ppm sodium and no more than about 500 ppm iron, preferably no more than 300 ppm iron. The alumna binder is a high purity alumina such as "catapal alumina." Preferably, the alumina binder is characterized in terms of an unusually high pore size and unusually low sodium content. As noted previously, the silicalite itself has a low sodium content in its crystalline structure. By maintaining a low sodium content in the alumina, a high portion of the catalyst sites in the silicalite structure are maintained in the active hydrogen form—that is, the low sodium content of the binder tends to minimize neutralization of the crystalline catalyst sites due to ion exchange between sodium in the binder and the acid sites in the catalyst. The alumina binder is further characterized in terms of a relatively large pore size after the catalyst is extruded and divided into particles. Specifically, the pore size of the binder, which can be termed the "maximum" pore size to avoid confusion with the pore size of the silicalite itself, is about 1,000 angstroms or more. A preferred pore size range is within the range of about 1,000 to about 1,800 angstroms. This relatively large pore size binder can enhance the efficiency of the catalyst by avoiding, or at least minimizing, an alumina-diffusing mechanism as applied to the catalyst particles themselves, thus enhancing access to the silicalite molecular sieve within the catalyst particles. The pore size of the molecular sieve structure itself normally can be expected to be on the order of about 5–6 angstroms. The silicalite catalyst preferably contains only a small amount of sodium, about 70–200 ppm sodium and contains only a small amount of iron, about 200–500 ppm. The catalyst need not contain any additional "promoter" metals incorporated during the synthesis of the catalyst.

Turning now to the drawings and referring first to FIG. 1, there is illustrated a schematic block diagram of an alkylation/transalkylation process carried out in accordance with the present invention. As shown in FIG. 1, a product stream comprising a mixture of ethylene and benzene in a mole ratio of benzene to ethylene about 10 to 20 is supplied via line 1 through a heat exchanger 2 to an alkylation zone 4. Alkylation zone 4 comprises one or more multi-stage reactors having a plurality of series-connected catalyst beds containing the preferred high silica/alumina ratio silicalite as described herein. The alkylation zone 4 is operated at temperature and pressure conditions to maintain the alkylation reaction in the vapor phase, ie. the aromatic substrate is in the vapor phase, and at a feed rate to provide a space velocity enhancing diethylbenzene production while retarding xylene production.

All or part of the output from the first alkylation reactor is supplied to a second liquid phase alkylation reactor 4A. Preferably, all of the output from the gas phase alkylation reactor is supplied to the liquid phase alkylation reactor, and this embodiment of the invention is depicted in FIG. 1. As shown, the output from the first alkylation reactor is supplied via line 5 to the second alkylation reactor 4A. Ethylene is supplied to the second alkylation reactor via line 3. The second alkylation reactor may take the form of a multistage reactor, similarly as described above with respect to reactor 4, the exception being that the second reactor is operated in the liquid (or the supercritical) phase and preferably is operated with a someone larger pore size molecular sieve.

The output from the second alkylation reactor 4A is supplied via line 5A to a intermediate benzene separation zone 6 which may take the form of one or more distillation columns. Benzene is recovered through line 8 and recycled through line 1 to the first alkylation reactor. Alternatively, a portion or all of the benzene recovered through line 8 may be supplied to line 5 where it is supplied directly to the second liquid phase alkylation reactor, bypassing the first gas phase alkylation reactor. Most likely, the benzene of line 1 is combined with line 8 and then portions of the combined stream are fed to units 4 and 4A. The bottoms fraction from the benzene separation zone 6, which includes ethylbenzene and polyalkylated benzenes including polyethylbenzene and xylene, is supplied via line 9 to an ethylbenzene separation zone 10. The ethylbenzene separation zone may likewise comprise one or more sequentially-connected distillation columns. The ethylbenzene is recovered through line 12 and applied for any suitable purpose, such as in the production of vinylbenzene. The bottoms fraction from the ethylbenzene separation zone 10 which comprises polyethylbenzene, principally diethylbenzene, is supplied via line 14 to a transalkylation reactor 16. Benzene is supplied to the transalkylation reaction zone through line 18. The transalkylation reactor, which preferably is operated under liquid phase conditions, contains a molecular sieve catalyst, preferably zeolite-Y, which has a somewhat larger pore size than the silicalite catalyst used in the first gas phase alkylation reaction zone. The output from the transalkylation reaction zone is recycled via line 20 to the benzene separation zone 6.

Figure 2:
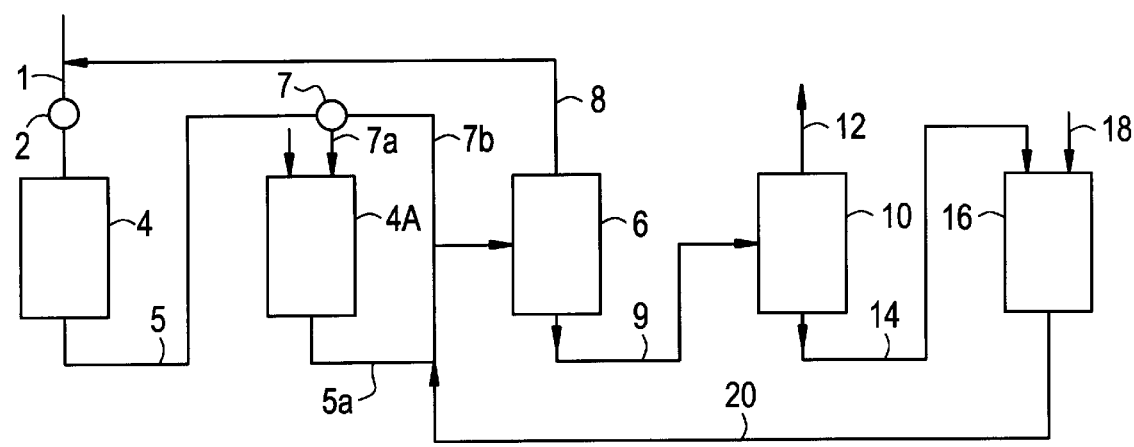
FIG. 2 is a schematic diagram of a modification of the process depicted in FIG. 1.

FIG. 1 illustrates the embodiment of the invention in which all of the output from the first vapor phase alkylation reactor is supplied to the second liquid phase alkylation reactor. This usually will be the preferred embodiment of the invention. However, in an alternative embodiment of the invention, the output from the vapor phase alkylation reactor is split so that part of it is supplied to the second liquid phase alkylation reactor with another part supplied to the benzene separation zone 6. This embodiment of the invention is illustrated in FIG. 2 in which like components are designated by the same reference numerals as used in FIG. 1. As shown in FIG. 2, the output from the vapor phase alkylation reactor is supplied via line 5 to a proportioning valve 7. The proportioning valve 7 is operated to split the output in line 5 with a portion of it supplied via line 7a to reactor 4A and the remaining supplied via line 7b to benzene separation zone 6. In operating in accordance with this embodiment of the invention, it will be preferred to supply a major portion of the product in line 5 to the second liquid phase alkylation reactor 4 and a minor portion via line 7b to benzene separation zone 6. More specifically, the amount supplied via line 7a to liquid phase alkylation reactor 4A will be within the range of 80–100 wt. % of the output from reactor 4, and the amount supplied via 7b to the benzene separation zone will be in an amount within the range of about 0–20 wt. %.

In either of the embodiments of FIGS. 1 and 2, the liquid phase alkylation reactor will normally be operated at a temperature well below the temperature of the gas phase alkylation reactor. Accordingly, the output of the gas phase reactor will be passed through a heat exchange zone (not shown) in which the product stream is cooled to a level resulting in a liquid phase product at the pressure of the liquid phase alkylation reactor. Depending upon the pressure involved in the liquid phase alkylation reactor, the heat exchange step can also be incorporated with a compression step where it is necessary to pressurize the feed to the liquid phase alkylation reactor to a value greater than the pressure in the gas phase alkylation reactor.

Figure 3:
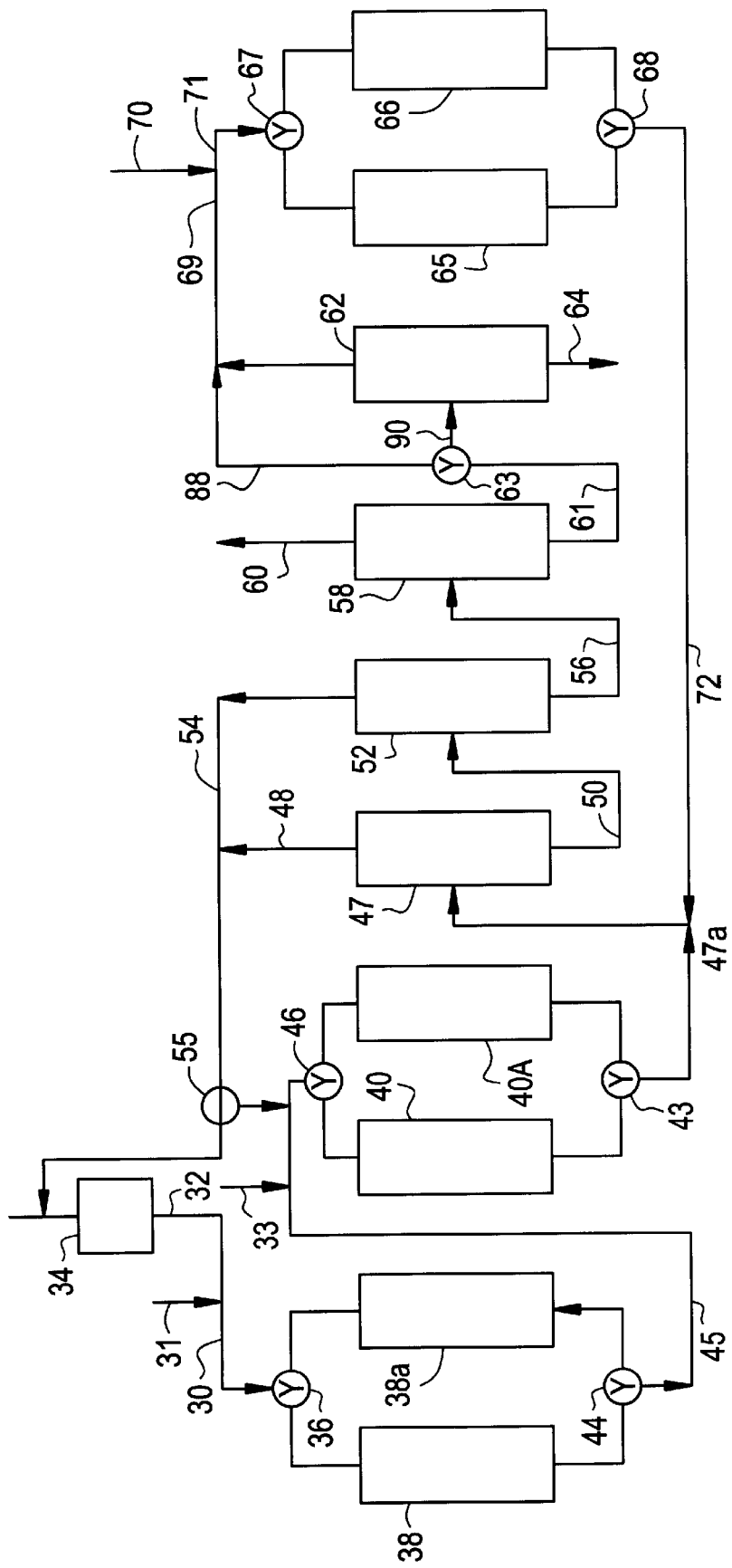
FIG. 3 is a schematic illustration of a preferred embodiment of the invention incorporating separate parallel-connected alkylation and transalkylation reactors with an intermediate multi-stage recovery zone for the separation and recycling of components.

Referring now to FIG. 3, there is illustrated in greater detail a suitable system incorporating a multi-stage intermediate recovery zone for the separation and recycling of components involved in the vapor phase alkylation, liquid phase alkylation, and alkylation/transalkylation process. As shown in FIG. 3, an input feed stream is supplied by fresh ethylene through line 31 and fresh benzene through line 32. Line 32 is provided with a preheater 34 to heat the benzene stream consisting of fresh and recycled benzene to the desired temperature for the alkylation reaction. The feedstream is applied through a two-way, three-position valve 36 and inlet line 30 to the top of one or both parallel vapor phase alkylation reaction zones 38 and 38A comprising a plurality of series connected catalyst beds each of which contains a silicalite alkylation catalyst. The reactors are operated at an average temperature, preferably within the range of 700° F.–800° F. inlet temperature and at pressure conditions of about 200 to 450 psia, to maintain the benzene in the gaseous phase.

In normal operation of the system depicted in FIG. 3, both reaction zones 38 and 38A may, during most of a cycle of operation, be operated in a parallel mode of operation in which they are both in service at the same time. In this case, valve 36 is configured so that the input stream in line 30 is roughly split in two to provide flow to both reactors in approximately equal amounts. Periodically, one reactor can be taken off-stream for regeneration of the catalyst. Valve 36 is then configured so that all of the feedstream from line 30 can be supplied to reactor 38 while the catalyst beds in reactor 38A are regenerated and visa versa. The regeneration procedure will be described in detail below but normally will take place over a relatively short period of time relative to the operation of the reactor in parallel alkylation mode. When regeneration of the catalyst beds in reactor 38A is completed, this catalyst can then be returned on-stream, and at an appropriate point, the reactor 38 can be taken off-stream for regeneration. This mode of operation in operation of the individual catalyst beds at relatively lower space velocities for prolonged periods of time with periodic relatively short periods of operation at enhanced, relatively higher space velocities when one reactor is taken off-stream. By way of example, during normal operation of the system with both reactors 38 and 38A on-stream, the feedstream is supplied to each reactor to provide a space velocity of about 32 hr.$^{-1}$ LHSV. When reactor 38A is taken off-stream and the feed rate continues unabated, the space velocity for reactor 38 will approximately double to 64 hr.$^{-1}$ LHSV. When the regeneration of reactor 38A is completed, it is placed back on-stream, and again the feed stream rate space velocity for each reactor will decrease to 35 hr.$^{-1}$ until such point as reactor 38 is taken off-stream, in which case the flow rate to reactor 38A will, of course, increase, resulting again in a transient space velocity in reactor 20 of 70 hr$^{-1}$ LHSV.

Figure 4:
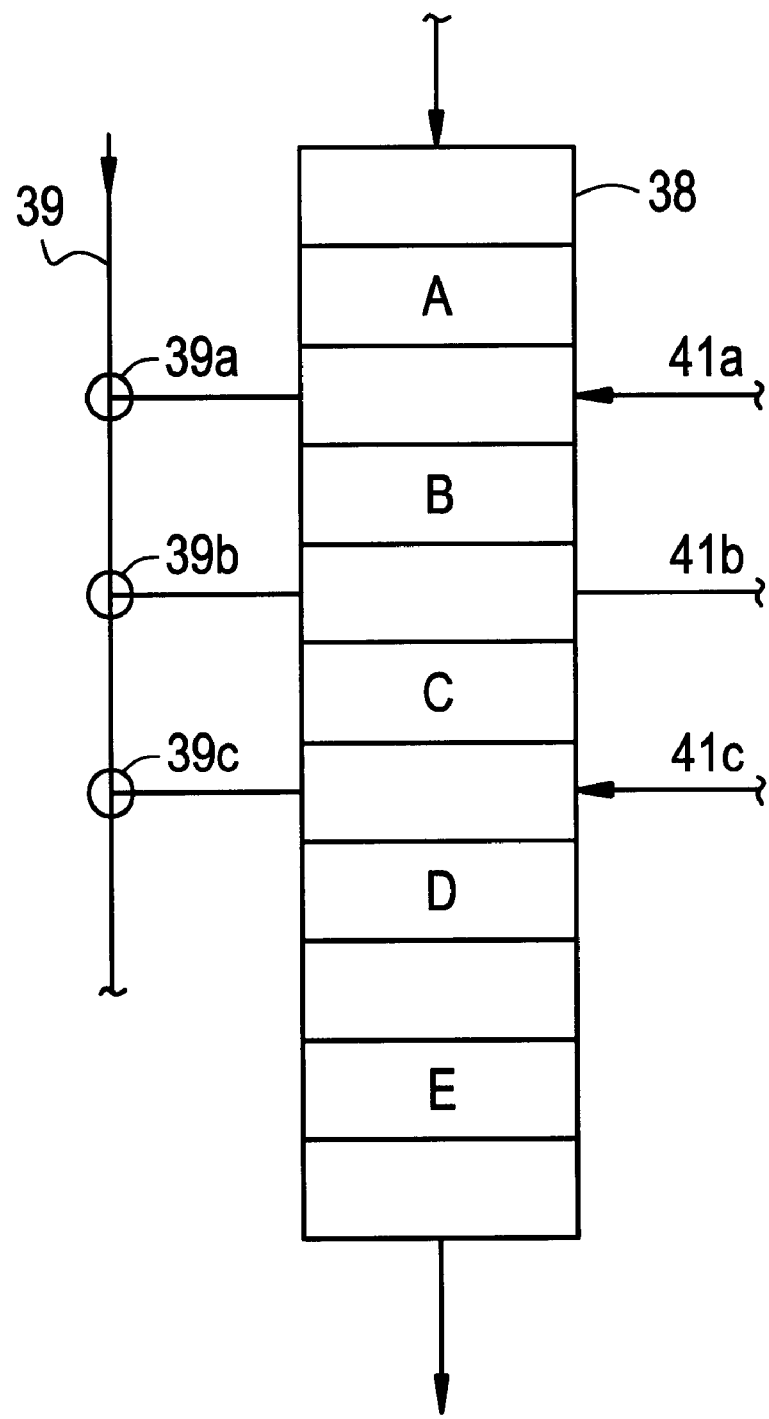
FIG. 4 is a schematic illustration of an alkylation zone comprising a plurality of series-connected catalyst beds with the interstage injection of feed components.

A preferred reactor configuration is shown in detail in FIG. 4. As illustrated there, the reactor 38 comprises five series connected catalyst beds designated as beds A, B, C, D, and E. An ethylene feed stream is supplied via line 39 and proportionating valves 39a, 39b and 39c to provide for the appropriate interstage injection of ethylene. Benzene can also be introduced between the catalyst stages by means of secondary benzene supply lines 41a, 41b and 41c, respectively. As will be recognized, the parallel reactor 38A will be configured with similar manifolding as shown in FIG. 4 with respect to reactor 38.

Returning to FIG. 3, the effluent stream from one or both of the alkylation reactors 38 and 38A is supplied through a two-way, three-position outlet valve 44 and outlet line 45 to a second set of liquid phase alkylation reactors 40 and 40a. The flow scheme shown in FIG. 3 corresponds to the preferred embodiment illustrated schematically in FIG. 1 in which all of the product stream from the vapor phase alkylation reaction zone is supplied to the liquid phase alkylation zone. Thus, the output in line 45 along with ethylene supplied via line 33 is supplied to one or both of liquid phase reactors 40 and 40a through a two-way through position inlet value 46. The liquid phase alkylation reactors 40 and 40a are typically operated under temperature conditions of about 300–600° F. with an average pressure of about 500–800 psia. As noted previously, the molecular sieve aromatic alkylation catalyst employed in the liquid phase alkylation reactors has a pore size greater than the average pore size of the silicalite molecular sieve employed in the first set of alkylation reactors. The zeolite employed in the liquid phase alkylation reactors preferably is zeolite Y or zeolite beta (including lanthanum beta) or a mixture of zeolite Y and zeolite beta. As noted previously, the catalyst employed in the second set of liquid phase alkylation reactors, preferably a zeolite beta or zeolite lanthanum beta. As indicated previously, the second set of liquid phase alkylation reactors can also be operated in the supercritical region, but for purposes of the present discussion, it will be assumed that the second set of alkylation reactors are operated in the liquid phase region which usually will be preferred.

The second set of alkylation reactors 40 and 40a can be operated in a parallel and intermittent regeneration mode, similarly as described above, with respect to reactors 38 and 38A. Thus, the proportioning valve 46 normally will be configured so that the product stream 45 is split in roughly equal proportions to provide parallel flow to both reactors 40 and 40a in approximately equal amounts. When the catalyst in one of the reactors requires regeneration, this reactor can be taken off-stream, and valve 46 can be configured to supply all of the product stream in line 45 to the other reactor. This will result in a rough doubling of space velocity in the liquid phase reactors similarly, as described above with respect to the first set of reactors.

The output from liquid phase alkylation reactors 40 and 40a is supplied through a two-way, three position outlet valve 43 via line 47a to a two-stage benzene recovery zone which comprises as the first stage a prefractionation column 47. Column 47 is operated to provide a light overhead fraction including benzene which is supplied via line 48 to the input side of heater 34 where it is mixed with benzene in line 32 and then to the alkylation reactor input line 30. A heavier liquid fraction containing benzene, ethylbenzene and polyethylbenzene is supplied via line 50 to the second stage 52 of the benzene separation zone. Stages 47 and 52 may take the form of distillation columns of any suitable type, typically, columns having from about 20–60 trays. The overheads fraction from column 52 contains the remaining benzene which is recycled via line 54 and line 48 to the alkylation reactor input. Thus, lines 48 and 54 correspond to the output line 8 of FIG. 1. The combined flow in lines 48 and 54 pass through a diverter valve 55 which can be employed to divert part or even all of the recycled benzene to the second liquid phase alkylation zone. Thus, the benzene recycle can be directed completely to the first set of alkylation reactors which will be the normal mode of operation, or it can be partially diverted to the second set of alkylation reactors 40 and 40a. In rare instances all of the combined benzene recycled stream in lines 48 and 54 can be recycled through valve 55 to input valve 46 of the second set of liquid phase alkylation reactors. The heavier bottoms fraction from column 52 is supplied via line 56 to a secondary separation zone 58 for the recovery of ethylbenzene. The overheads fraction from column 58 comprises relatively pure ethylbenzene which is supplied to storage or to any suitable product destination by way of line 60. By way of example, the ethylbenzene may be used as a feedstream to a styrene plant in which styrene is produced by the dehydrogenation of ethylbenzene. The bottoms fraction containing polyethylbenzenes, heavier aromatics such as cumene and butylbenzene, and normally only a small amount of ethylbenzene is supplied through line 61 to a tertiary polyethylbenzene separation zone 62. As described below, line 61 is provided with a proportioning valve 63 which can be used to divert a portion of the bottoms fraction directly to the transalkylation reactor. The bottoms fraction of column 62 comprises a residue which can be withdrawn from the process via line 64 for further use in any suitable manner. The overhead fraction from column 62 comprises a polyalkylated aromatic component containing diethylbenzene and triethylbenzene (usually in relatively small quantities) and a minor amount of ethylbenzene is supplied to an on stream transalkylation reaction zone. Similarly as described above with respect to the alkylation reactors, parallel transalkylation reactors 65 and 66 are provided through inlet and outlet manifolding involving valves 67 and 68. Both of reactors 65 and 66 can be placed on stream at the same time so that both are in service in a parallel mode of operation. Alternatively, only one transalkylation reactor can be on-stream with the other undergoing regeneration operation in order to bum coke off the catalyst beds by minimizing the amount of ethylbenzene recovered from the bottom of column 58, the ethylbenzene content of the transalkylation feedstream can be kept small in order to drive the transalkylation reaction in the direction of ethylbenzene production. The polyethylbenzene fraction withdrawn overhead from column 62 is supplied through line 69 and mixed with benzene supplied via line 70. This mixture is then supplied to the on-line transalkylation reactor 65 via line 71. Preferably, the benzene feed supplied via line 70 is of relatively low water content, about 0.05 wt. % or less.

Preferably, the water content is reduced to a level of about 0.02 wt. % or less and more preferably to no more than 0.01 wt. %. The transalkylation reactor is operated as described before in order to maintain the benzene and alkylated benzenes within the transalkylation reactor in the liquid phase. Typically, the transalkylation reactor may be operated to provide an average temperature within the transalkylation reactor of about 150° F.–550° F. and an average pressure of about 600 psi. The preferred catalyst employed in the transalkylation reactor is zeolite Y having the characteristics described previously. The weight ratio of benzene to polyethylbenzene should be at least 1:1 and preferably is within the range of 1:1 to 4:1.

The output from the transalkylation reactor or reactors containing benzene, ethylbenzene, and diminished amounts of polyethylbenzene is recovered through line 72. Typically, line 72 will be connected to the inlet lines 47a for recycle to the prefractionation column 47 as shown. However, the effluent from the liquid-phase transalkylation reactor may be supplied to either or both of distillation columns 47 and 52. Preferably, the system will be operated in a manner in which all or most of the liquid phase alkylation product is supplied to column 47 as shown.

Returning to the operation of the separation system, in one mode of operation the entire bottoms fraction from the ethylbenzene separation column 58 is applied to the tertiary separation column 62 with overhead fractions from this zone then applied to the transalkylation reactor. This mode of operation offers the advantage of relatively long cycle lengths of the catalyst in the transalkylation reactor between regeneration of the catalyst to increase the catalyst activity. Another mode of operation of the invention achieves this advantage by supplying a portion of the output from the ethylbenzene separation column 58 through valve 63 directly to the transalkylation reactor. By employing vapor phase alkylation with subsequent liquid phase alkylation in combination with liquid phase transalkylation in accordance with the present invention, a significant quantity of the bottoms fraction from the ethylbenzene column can be sent directly to the transalkylation reactor, thus decreasing the amount of residue which is lost from the process. This mode of operation is consistent with and particularly advantageous in combination with the operation of the alkylation reaction zone to retard transalkylation and enhance ethylbenzene production. By employing the second stage liquid phase alkylation reactor, sufficient additional alkylation of the ethylene is accomplished to provide an increase in the amount of ethylbenzene withdrawn from the ethylbenzene column 58 without a corresponding increase in the capacity of the fractionation columns involved in the intermediate recovery zone.

As shown in FIG. 3, a portion of the bottoms fraction from the secondary separation zone 58 bypasses column 62 and is supplied directly to the transalkylation reactor 65 via valve 63 and line 88. A second portion of the bottoms fraction from the ethylbenzene column is applied to the tertiary separation column 62 through valve 63 and line 90. The overhead fraction from column 62 is commingled with the bypass effluent in line 88 and the resulting mixture is fed to the transalkylation reactor via line 67. By bypassing the column 62 with a substantial portion of the bottoms product from column 58, the residue which is lost from the system can be reduced. Preferably in this mode of operation a substantial amount of the bottoms product from column 58 is sent directly to the transalkylation reactor, bypassing the polyethylbenzene column 62. Normally, the weight ratio of the first portion supplied via line 88 directly to the transalkylation reactor to the second portion supplied initially via line 90 to the polyethylbenzene would be within the range of about 1:2 to about 2:1. However, the relative amounts may vary more widely to be within the range of a weight ratio of the first portion to the second portion in a ratio of about 1:3 to 3:1.

As noted previously, it is preferred to follow the vapor phase alkylation reaction with a liquid phase alkylation reaction under relatively mild conditions. Notwithstanding the relatively mild conditions in the alkylation reactor, sufficient alkylation is accomplished to increase the ethylbenzene production above that achieved through the use of only a vapor phase alkylation reactor without requiring an increase in the capacity of the distillation equipment in the several recovery zones. While the relatively mild conditions of simple liquid phase operations are preferred, the present invention can be carried out with the second alkylation stage carried out in a quasi-liquid phase with the benzene substrate under more severe conditions in which both the temperature and the pressure are above the critical temperature and pressure for benzene to operate in the supercritical region. As noted previously, in this case the second phase alkylation reactor(s) would be operated at a temperature of about 290° C. or above and a pressure in excess of 700 psia. Somewhat higher temperatures and pressures would normally be employed. Here, operation of the second stage alkylation reactor in the critical phase with benzene in the supercritical region would be within the range of 300–350° C. and >650 psia.

Having described specific embodiments of the present invention, it will be understood that modifications thereof may be suggested to those skilled in the art, and it is intended to cover all such modifications as fall within the scope of the appended claims.

What is claimed is:

1. In the production of ethylbenzene, the method comprising:
   (a) providing a first alkylation reaction zone containing a molecular sieve aromatic alkylation catalyst:
   (b) supplying a feedstock containing benzene and ethylene to said first alkylation reaction zone;
   (c) operating said first alkylation reaction zone at temperature and pressure conditions in which benzene is in the gaseous phase to cause gas-phase ethylation of said benzene in the presence of said molecular sieve catalyst to produce an alkylation product comprising a mixture of benzene and ethylbenzene;
   (d) recovering said alkylation product from said first reaction zone and supplying at least a portion of said product from said first reaction zone to a second alkylation reaction zone containing a molecular sieve aromatic alkylation catalyst;
   (e) supplying ethylene to said second alkylation reaction zone;
   (f) operating said second alkylation reaction zone at temperature and pressure conditions in which benzene is in the liquid phase or in the supercritical phase to cause ethylation of said benzene in the presence of said second molecular sieve to produce an alkylation product comprising a mixture of benzene and ethylbenzene;
   (g) recovering the alkylation product from said second alkylation reaction zone and supplying said product from said second alkylation reaction zone to a recovery zone for the separation of benzene and the separation and recovery of ethylbenzene from the alkylation product; and (h) recycling benzene recovered from said recovery zone to at least one of said first and second alkylation reaction zones.

2. The method of claim 1 wherein substantially all of the alkylation product recovered from said first alkylation reaction zone is supplied to said second alkylation reaction zone.

3. The method of claim 1 wherein a first portion of said product from said first alkylation reaction zone is supplied to said second alkylation reaction zone and a second portion of said product from said first alkylation reaction zone bypasses said second alkylation reaction zone and is supplied directly to said recovery zone.

4. The method of claim 1 wherein the molecular sieve catalyst in said first alkylation reaction zone is a small to intermediate pore size molecular sieve and the molecular sieve catalyst in said second aromatic alkylation zone is an intermediate pore size molecular sieve having an effective pore size greater than the effective pore size of the catalyst in said first alkylation reaction zone.

5. The method of claim 4 wherein said catalyst in said second alkylation reaction zone is zeolite beta or zeolite La-Beta.

6. The method of claim 1 wherein the molecular sieve catalyst in said first alkylation reaction zone is monoclinic silicalite having a silica/alumina ratio greater than 250 and the catalyst in said second alkylation reaction zone is selected from the group consisting of zeolite Y, zeolite omega, zeolite beta, and zeolite lanthanum beta.

7. The method of claim 1 wherein at least a major portion of said recycled benzene is recycled to said first alkylation reaction zone.

8. The method of claim 1 wherein said catalyst in said first alkylation reaction zone is silicalite having a silica/alumina ratio of at least 275.

9. The method of claim 8 wherein said silicalite catalyst is monoclinic silicalite having an average crystal size of less than one micron.

10. The method of claim 9 wherein said monoclinic silicalite alkylation catalyst has an average crystal size of about 0.5 microns or less and is formulated with an alumna binder to provide catalyst particles having a surface area/volume ratio of at least 50 in.$^{-1}$.

11. In the production of ethylbenzene and the separate transalkylation of polyethylbenzene, the method comprising:

(a) providing a first alkylation reaction zone containing a molecular sieve aromatic alkylation catalyst:

(b) supplying a feedstock containing benzene and ethylene to said first alkylation reaction zone;

(c) operating said first alkylation reaction zone at temperature and pressure conditions in which benzene is in the gaseous phase to cause gas-phase ethylation of said benzene in the presence of said molecular sieve catalyst to produce an alkylation product comprising a mixture of benzene, ethylbenzene, and a polyalkylated aromatic component;

(d) recovering said alkylation product from said first reaction zone and supplying at least a portion of said product from said first reaction zone to a second alkylation reaction zone containing a molecular sieve aromatic alkylation catalyst;

(e) supplying ethylene to said second alkylation reaction zone;

(f) operating said second alkylation reaction zone at temperature and pressure conditions in which benzene is in the liquid phase or in the supercritical phase to cause ethylation of said benzene in the presence of said second molecular sieve to produce an alkylation product comprising a mixture of benzene, ethylbenzene, and a polyalkylated aromatic component;

(g) recovering the alkylation product from said second alkylation reaction zone and supplying at least a portion said product from said second alkylation reaction zone to an intermediate recovery zone for the separation and recovery of ethylbenzene from the alkylation product and the separation and recovery of a polyalkylated aromatic component including diethylbenzene;

(h) supplying at least a portion of said polyalkylated aromatic component including diethylbenzene in said polyalkylated component to a transalkylation zone containing a molecular sieve transalkylation catalyst;

(i) supplying benzene to said transalkylation reaction zone;

(j) operating said transalkylation reaction zone under temperature and pressure conditions to cause disproportionation of said polyalkylated aromatic fraction to produce a disproportionation product containing unreacted benzene and having a reduced diethylbenzene content and an enhanced ethylbenzene content.

12. The method of claim 11 wherein at least a portion of said disproportionation product is supplied to said intermediate recovery zone.

13. The method of claim 11 wherein the molecular sieve catalyst in said first alkylation reaction zone is a small to intermediate pore size molecular sieve and the molecular sieve catalyst in said second aromatic alkylation zone and the molecular sieve catalyst in said transalkylation reaction zone are each an intermediate pore size molecular sieve having an effective pore size greater than the effective pore size of the catalyst in said first alkylation reaction zone.

14. The method of claim 11 wherein the molecular sieve catalyst in said first alkylation reaction zone is monoclinic silicalite having a silica/alumina ratio greater than 250 and the catalyst in said second alkylation reaction zone is selected from the group consisting of zeolite Y, zeolite beta, and zeolite lanthanum beta.

15. The process of claim 14 wherein said transalkylation reaction zone contains a zeolite Y transalkylation catalyst and is operated under temperature and pressure conditions effective to maintain the feed stock in said transalkylation zone in the liquid phase.

16. The process of claim 15 wherein said second alkylation zone contains zeolite beta or zeolite La-Beta.

17. In the production of ethylbenzene, the method comprising:

(a) providing a first alkylation reaction zone containing a molecular sieve aromatic alkylation catalyst comprising monoclinic silicalite having an average crystal size of less than one micron and a silica/alumina ratio of at least 250;

(b) supplying a feedstock containing benzene and ethylene to said first alkylation reaction zone;

(c) operating said first alkylation reaction zone at temperature and pressure conditions in which benzene is in the gaseous phase to cause gas-phase ethylation of said benzene in the presence of said molecular sieve catalyst to produce an alkylation product comprising a mixture of benzene and ethylbenzene;

(d) recovering said first alkylation product from said first reaction zone and supplying at least a portion of said product from said first reaction zone to a second alkylation reaction zone containing an intermediate molecular sieve aromatic alkylation catalyst having an effective pore size greater than the effective pore size of said silicalite in said first alkylation reaction zone;

(e) supplying ethylene to said second alkylation reaction zone;

(f) operating said second alkylation reaction zone at temperature and pressure conditions in which benzene is in the liquid phase or in the supercritical phase to cause ethylation of said benzene in the presence of said second molecular sieve to produce an alkylation product comprising a mixture of benzene and ethylbenzene; and (g) recovering the alkylation product from said second alkylation reaction zone and supplying said product from said second alkylation reaction zone to a recovery zone for the separation and recovery of ethylbenzene from the alkylation product;

(h) recycling benzene recovered from said recovery zone to at least one of said first and second alkylation reaction zones.

18. The method of claim 17 wherein the catalyst in said second alkylation reaction zone is selected from the group consisting of zeolite Y, zeolite beta, and zeolite lanthanum beta.

19. The method of claim 18 wherein said catalyst in said second alkylation reaction zone is zeolite beta or zeolite La-Beta.

20. The method of claim 19 wherein said silicalite alkylation catalyst has an average crystal size of about 0.5 microns or less and is formulated with an alumina binder to provide catalyst particles having a surface area/volume ratio of at least 50 in.$^{-1}$.

* * * * *